(12) United States Patent
Wicker et al.

(10) Patent No.: US 7,194,120 B2
(45) Date of Patent: Mar. 20, 2007

(54) METHODS AND SYSTEMS FOR IMAGE-GUIDED PLACEMENT OF IMPLANTS

(75) Inventors: Ryan B. Wicker, El Paso, TX (US); Buzuayehu Tedla, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/448,263

(22) Filed: May 29, 2003

(65) Prior Publication Data

US 2004/0240715 A1 Dec. 2, 2004

(51) Int. Cl.
*G06K 9/00* (2006.01)

(52) U.S. Cl. ...................................... 382/128
(58) Field of Classification Search ................ 382/128, 382/173, 300, 199; 378/42, 54; 600/407, 600/425, 426, 427
See application file for complete search history.

(56) References Cited

U.S. PATENT DOCUMENTS

| | | | | |
|---|---|---|---|---|
| 5,291,537 A | 3/1994 | Mazess | | 378/54 |
| 5,682,886 A | 11/1997 | Delp et al. | | 600/407 |
| 5,748,767 A | 5/1998 | Raab | | 382/128 |
| 5,768,134 A | 6/1998 | Swaelens et al. | | 700/121 |
| 5,772,594 A | 6/1998 | Barrick | | 600/407 |
| 5,799,055 A | 8/1998 | Peshkin et al. | | 378/42 |
| 5,850,836 A | 12/1998 | Steiger et al. | | 600/300 |
| 5,871,018 A | 2/1999 | Delp et al. | | 128/898 |
| 5,951,475 A | * 9/1999 | Gueziec et al. | | 600/425 |
| 6,002,959 A | 12/1999 | Steiger et al. | | 600/425 |
| 6,069,932 A | 5/2000 | Peshkin et al. | | 378/42 |
| 6,167,296 A | 12/2000 | Shahidi | | 600/427 |
| 6,175,758 B1 | 1/2001 | Kambin | | 600/426 |
| 6,198,794 B1 | 3/2001 | Peshkin et al. | | 378/42 |
| 6,226,548 B1 | 5/2001 | Foley et al. | | 600/426 |
| 6,488,681 B2 | 12/2002 | Martin et al. | | 606/61 |
| 2004/0030245 A1 | 2/2004 | Noble et al. | | |

OTHER PUBLICATIONS

Cuppone et al., Design of Drill Guides for the Thoracic and Cervical Regions of the Spine, Jul. 2001, University of Leeds.*
Gautier et al. "Accuracy of Computer guided Screw Fixation Sacroiliac Joint" Clinical orthopaedics and related research No. 393, pp. 310-317. Dec. 2001.*
Kalfas et al., Application of frameless stereotaxy to pedicale screw fixation of the spine, J. Neurosurg. vol. 83, pp. 641-647, Oct. 1995.*
Merloz et al., Computer assisted spine surgery, Clinical orthopaedics and related research No. 337, pp. 86-96. Dec. 1997.*

* cited by examiner

*Primary Examiner*—Vikkram Bali
(74) *Attorney, Agent, or Firm*—Gardere Wynne Sewell LLP

(57) ABSTRACT

Methods and computer systems for determining the placement of an implant in a patient in need thereof comprising the step of analyzing intensity-based medical imaging data obtained from a patient, isolating an anatomic site of interest from the imaging data, determining anatomic spatial relationships with the use of an algorithm, wherein the algorithm is optionally automated.

37 Claims, 8 Drawing Sheets

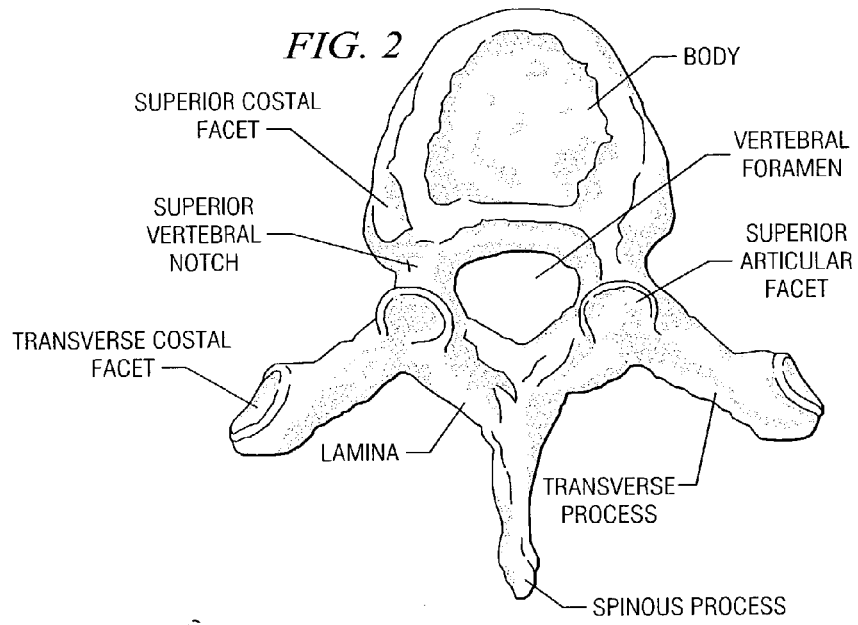
FIG. 2
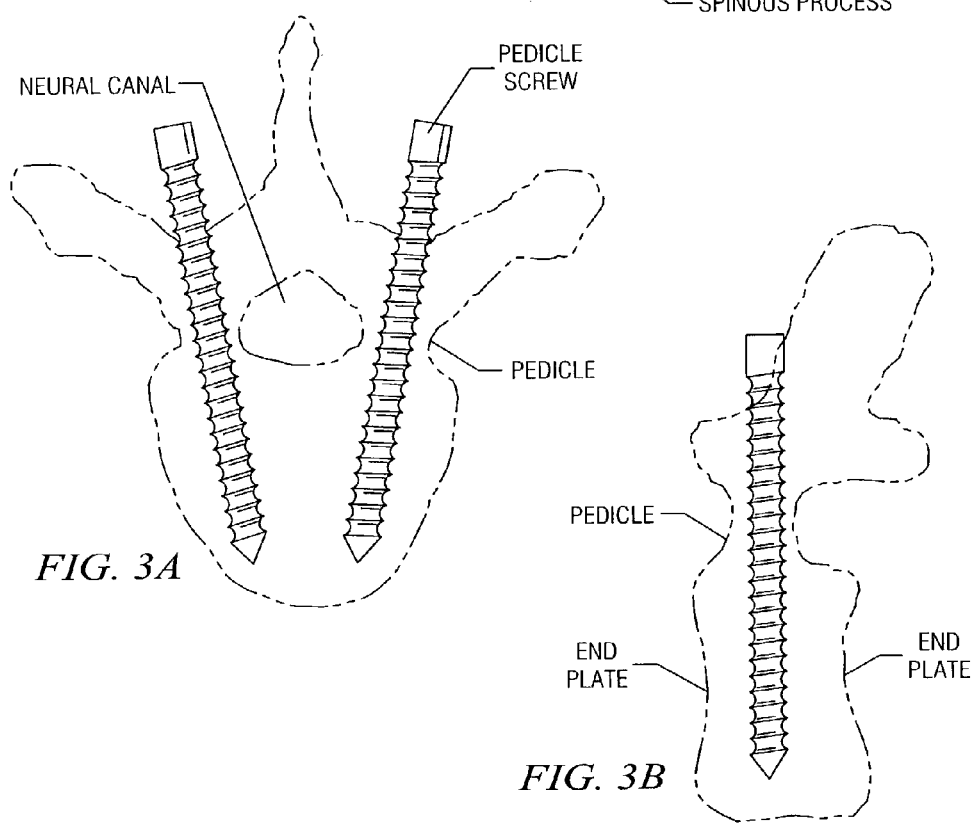
FIG. 3A
FIG. 3B

METHODS AND SYSTEMS FOR IMAGE-GUIDED PLACEMENT OF IMPLANTS

STATEMENT REGARDING FEDERALLY SPONSORED RESEARCH OR DEVELOPMENT

The present application was supported in part by the National Science Foundation grant number EIA-0080940. The government may have certain rights in the invention.

BACKGROUND OF THE INVENTION

The present invention relates to the general field of data processing, and more particularly, to methods and computer systems for image-guided placement of an implant or device at one or more anatomic sites.

The spinal column is a complex system of bones and connective tissues that provides support for the body and protects the spinal cord and associated nerves from damage. The spinal column is made up of a series of vertebra stacked upon one another. Situated between each vertebral body is an intervertebral disc that cushions and dampens compressive forces experienced by the spinal column. A vertebral canal containing the spinal cord passes down the length of the spinal column.

There are many types of spinal column maladies, including disorders caused by abnormalities, disease or trauma. These include ruptured or slipped discs, degenerative disc disease, fractured vertebra, and the like. Patients that suffer from such conditions often experience extreme and debilitating pain, as well as diminished nerve function.

A technique commonly referred to as spinal fixation or fusion is often the treatment of choice for such conditions. In such a procedure, surgical implants are used for fusing together and/or mechanically immobilizing vertebrae of the spine. Spinal fixation may also be used to alter the alignment of adjacent vertebrae relative to one another so as to change the overall alignment of the spine. Such techniques have been used effectively to treat the above-described conditions and, in most cases, to relieve pain suffered by the patient. However, as will be set forth in more detail, there are some disadvantages associated with current fixation devices, such as the lack of methods to accurately measure implant size and placement and the inability to reproduce measurements from patient to patient.

Current technology involves the manual determination of the appropriate size and placement of an implant such as a pedicle screws. If a mistake is made in selecting an appropriate size and/or orientation of the pedicle screw, the ramifications for the patient may be severe and cause great injury. Therefore, there remains a need to provide a method an system for accurately determining implant placement (e.g., determining optimum trajectory, diameter and depth of placement for an implant). In addition, such a method and system should be reproducible, be available to automatic use and should provide patient-specific data to alleviate damage or injury to the patient.

SUMMARY OF THE INVENTION

The invention described herein is a method and computer system for accurate determination of anatomic indices on a patient using medical imaging data obtained from one or more medical imaging devices such as computed tomography (CT), magnetic resonance imaging (MRI), positron emission tomography (PET), stereotactic ultrasound, endoscopic ultrasound, as examples. The present invention relates to the first step that is generally used in, for example, spinal fixation, namely the placement of a surgical implant such as a screw (e.g., pedicle screw) into a portion of one or more vertebra through the pedicles. For this example, the pedicle screws are used to anchor other surgical devices used in a variety of surgical procedures relating to the spine. The screws must be placed with precision to avoid damaging underlying structure, such as the spinal cord, however, they must be strong enough and anchored sufficiently well to allow them to serve as effective anchors. Therefore the present invention provides for a method and system of determining the proper size and orientation of an implant for a patient in need thereof, for example in an operating room. In accordance with one aspect of the present invention, a method for determining the placement of pedicle screws is provided by determining a trajectory for the placement of a pedicle screw in a patient with the use of an algorithm based on medical imaging data obtained from the patient.

The present invention replaces "best-guess" procedures and inconsistent determinations for highly technical medical and surgical procedures. One advantage with the present invention as described herein is that it serves as a cost-effective image-guided placement system providing precise and reproducible data for use in medical procedures, such as surgical implantation, tumor detection, pedicle screw insertion, etc. As such, the methods and computer systems of the present invention serve as powerful tools to automatically obtain anatomic data about a site and use it to accurately place a device and or implant as needed. Custom designed products of the present invention include computer systems and other technologies for use in medicine, engineering, modeling systems, robotics, and other biotechnology applications, as examples.

Those skilled in the art will further appreciate the above-mentioned advantages and superior features of the invention, together with other important aspects thereof upon reading the detailed description that follows in conjunction with the drawings.

BRIEF DESCRIPTION OF THE SEVERAL VIEWS OF THE DRAWINGS

For a more complete understanding of the features and advantages of the present invention, reference is now made to the detailed description of the invention along with the accompanying FIGURES in which corresponding numerals in the different FIGURES refer to corresponding parts and in which:

FIG. 2 depicts an example of a three-dimensional (3D) vertebral image of the sixth thoracic vertebra with labeled points of interest;

FIG. 3 illustrates the insertion paths for an implant such as a pedicle screw at an anatomic site such as a vertebra;

DETAILED DESCRIPTION OF THE INVENTION

Although making and using various embodiments of the present invention are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

As described herein, the present invention is a method and computer system with an algorithm for the automatic extraction of data about an anatomic site of interest (e.g., organ, tissue) in order to determine appropriate implant size and orientation. The present invention optimizes data extracted from any of a number of intensity-based medical imaging techniques in order to resolve the size, length, and trajectory of the implant to be used. The example provided below illustrates the use of the invention to optimize properties about a pedical screw to be placed in vertebrae of a patient in need thereof.

The present invention includes the following processes: importing data collected from one or more images of an anatomic site (e.g., images collected from CT, MRI, PET, ultrasound, as examples); pre-processing the data to ensure compatibility; isolating the anatomic area of interest, generally using thresholding segmentation calculations; defining the boundaries of the anatomic site of interest for each calculated plane; computing a minimum anatomic diameter, a maximum implant diameter, an optimum implant trajectory, and/or a maximum length of anatomic site for the optimum trajectory using search calculations that include geometric considerations.

In general, calculations of the present invention include the following steps: importation of medical imaging data; interpolation and data pre-processing; segmentation; boundary extraction of the anatomic site; anatomic site and implant identification (e.g., size determination); boundary determination of the implant (e.g., relative to the anatomic site); optimization of trajectory; maximization of anatomic site for optimum trajectory.

Importation of Medical Imaging Data

Using one method of the present invention, it is possible to automatically extract from imaging data the optimum implant insertion path (e.g., pedicle screw path) for surgical implantation (e.g., orthopaedic spinal pedicle screw insertion). Using this tool, in one embodiment, a surgeon may determine, before beginning a surgical procedure, the desired path as well as the size and length of the pedicle screw to insert.

Figure 1:
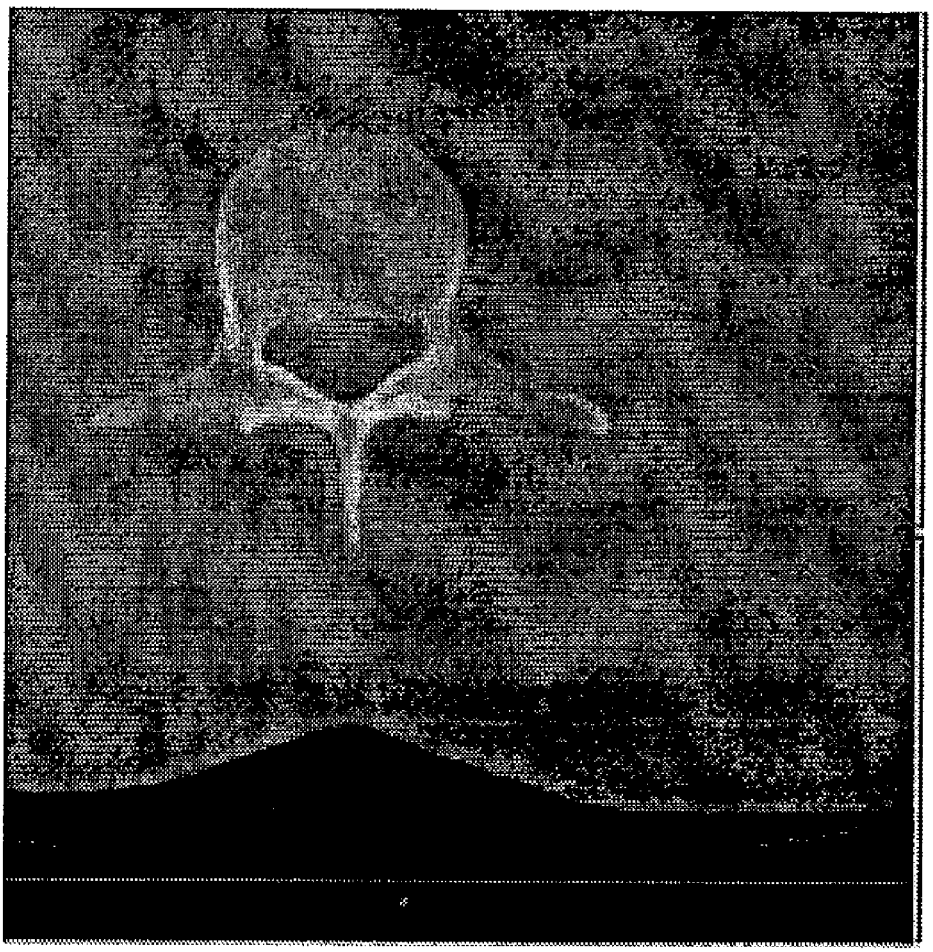
FIG. 1 depicts an example of a two-dimensional (2D) vertebral image of the lumbar spine with surrounding tissue taken by a CT imaging device.

The anatomic site must first be assessed. In this example, a vertebra from the spinal column is used. The vertebral column is about 70 cm (28 inches) long in an average adult. There are 24 vertebrae of the spine, with the first seven (beginning from the base of the skull and proceeding down the body) known as the cervical vertebrae, the next 12 vertebrae are known as the thoracic vertebrae, and the next 5 called the lumbar vertebrae. They are customarily designated as Cx, Tx, and Lx, corresponding to the cervical, thoracic, and lumbar sections, respectively, with "x" designating the segment number. FIG. 1 shows the typical 2D CT imaging slice of a lumbar spine segment taken of a patient.

Figure 4:
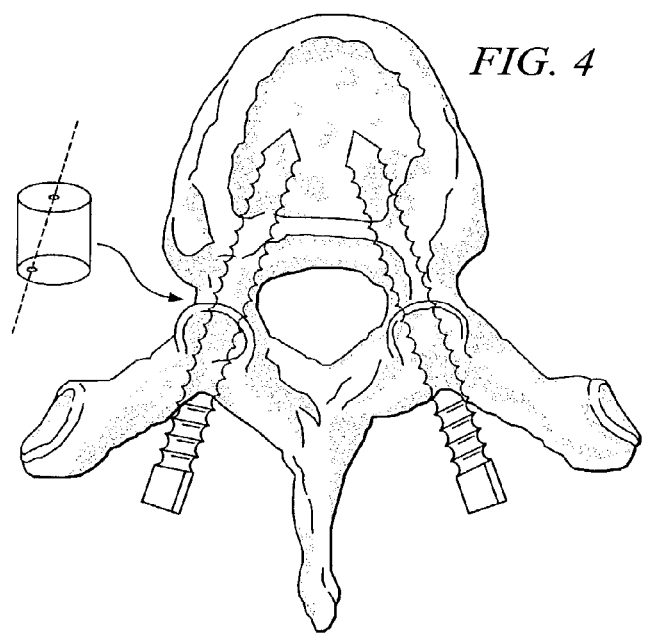
FIG. 4 depicts physical representation of an implant (e.g., pedicle screw) into an anatomic site (e.g., vertebra)

FIG. 1 depicts an image from a CT scan (an intensity-based image) used in accordance with the present invention. FIG. 2 depicts a physical image (a 3D view) of the sixth thoracic vertebra. FIGS. 3 and 4 provide representations of the cross-section of FIGS. 1 and 2 with implants (also referred to as pedicle screws and/or instruments) inserted within, illustrating the insertion paths.

Figure 5:
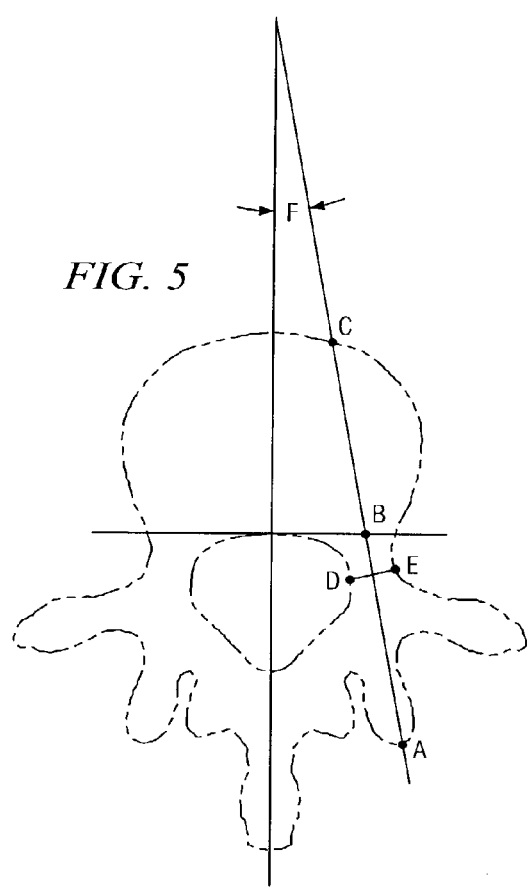
FIG. 5 is a typical boundary image showing the anatomic width DE of a pedicle, also referred to as the transverse pedicle width.

Once an anatomic site such as the vertebra is isolated, its boundary is extracted resulting in an image similar to that depicted in FIG. 5. Parameters from that image are, in one embodiment, computed, including the pedical length (AB), the chord length (AC), the transverse pedicle width (DE) and the transverse pedicle angle (F).

Using FIG. 5 as a reference, one embodiment of the present invention includes determining the minimum transverse pedicle width, DE, for all of the 2D image slices that contain the vertebra under study. The overall minimum transverse pedicle width for the vertebra under study is the minimum of the minimum transverse pedicle width for all of the image slices containing the vertebra. The optimum trajectory may be determined by performing a least squares fit or weighted least squares fit on the locus of mid-points for the minimum transverse pedicle widths for each slice, as will be described in more detail in the following. Once the optimum trajectory is determined, the maximum length of the anatomic site (e.g., bone and used here to determine the pedicle screw length) may be determined by identifying the intersection of the optimum trajectory with the boundary image.

If the optimum trajectory were assumed to lie in the image slice shown in FIG. 5, the maximum length of bone described above would correspond to the chord length, AC. This example is for illustrative purposes given that the optimum trajectory may traverse multiple slices. With the optimum trajectory, overall minimum transverse pedicle width, and maximum length of bone determined, the optimum trajectory and diameter and length of screw to be placed in the pedicle screw insertion medical procedure may be calculated automatically. Further implementation of this method is described in the following sections.

Interpolation and Preprocessing

Using CT slices in xy planes stacked in the z direction, such that the z direction is approximately collinear with the spine, and the xy plane is perpendicular to z, data for a given xy plane is assessed. Data for a given xy plane is referred to as a slice of data.

In order to determine the efficacy of determining pedicle screw placement with the present invention, the data are, in one embodiment, initially standardized for the pedicle width, length and trajectory determination. This preprocessing standardization uses interpolation in the z-direction to equalize the interslice distance. The step transforms a set of 2D data of differing inter-slice distances to one with uniform distances forming cubes or voxels. The preprocessing step enables comparisons to be made with images acquired with different medical imaging modalities (such as MRI scans or CT scans, as examples) with different interslice dimensions.

Interpolators used with the present invention may be scene-based or object-based. The scene-based methods use only grayscale information. The simplest of the scene-based methods is the nearest neighbor or zero order holds operation. Common higher order interpolations are linear interpolations and cubic interpolations. The object-based methods use available information of objects to enhance the interpolation. Another interpolation of the object-based method is called shape-based interpolation. In the present invention, the shape-based method may be employed as described in the following example.

Variables

V=3D scene k=grayscale value, k $\in$ K where K={kmin, kmax} f=function that assigns a grayscale value to each voxel.

f(x, y, z)=k

The algorithm may include the following steps:

1. Lifting

The 3D scene is transformed to a 4D binary scene $$f_L(x, y, z, k) = 1 \text{ if } f(x, y, z) > k$$
$$= 0 \text{ else}$$

2. A distance transform is performed.

3. Grayscale interpolation along the x, y, and z directions is performed.

4. Change all positive distances to 1 and all negative distances to 0.

5. Collapse. The inverse of uplifting and results in the grayscale scene $f_U$.

$f_U$ (x,y, z)=max {k |f(x, y, z)=1}.

Segmentation

Segmentation of 3D images is an operation that aims at partitioning the voxels into 3D regions that represent meaningful objects or features. Segmentation can be accomplished using a variety of methods.

The simplest segmentation is a point-based method and depends only on voxel characteristics (e.g. intensity). Such a procedure does not take into account proximity and connectivity. When this method is not sufficient one can consider other methods known as region-based techniques that involve region growing, region splitting, and region merging. Additionally, morphological algorithms can be used to enhance the process of segmentation.

Due to the large difference in physical density between soft tissue and bone, only a pair of intensity thresholds is typically sufficient to segment the spine. Voxel intensities that lie between some lower limit and some higher limit are assigned a value of 1 and those outside are assigned a value of 0. Segmentation of the spine can be done with simple thresholding (using only intensities). Using this method makes it necessary only to find the threshold limits. These limits change with different slices of the volume; histogram methods are generally used to identify these limits.

Boundary Extraction

Boundary extraction or detection is accomplished by locating the surface of the objects. This method works by marking points that make up the edges. Any of the edge detection techniques may be used, as are well known to one of ordinary skill in the art. Once extracted, the edges are joined to make line segments that are linked to form object boundaries.

Further Illustrative Examples

Figure 6A:
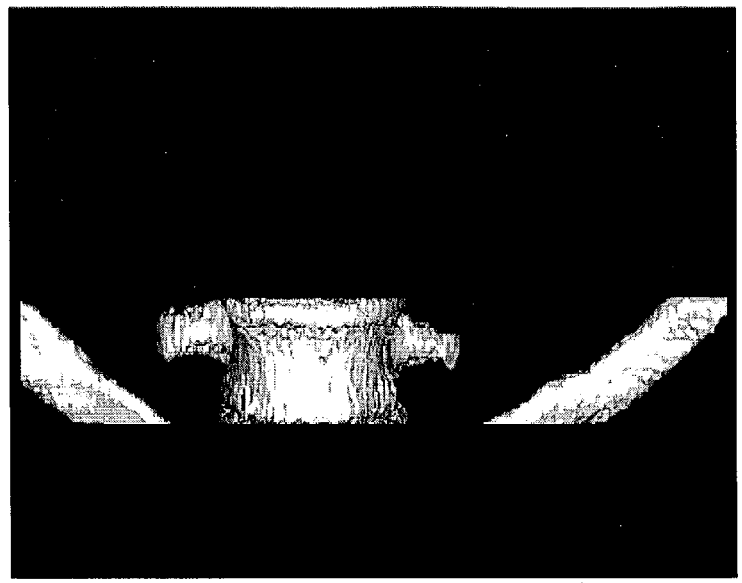
FIG. 6 depicts (A) a side view of segmented volume and (B) top view of segmented volume, both using CT imaging data with algorithms of the present invention.
Figure 6B:
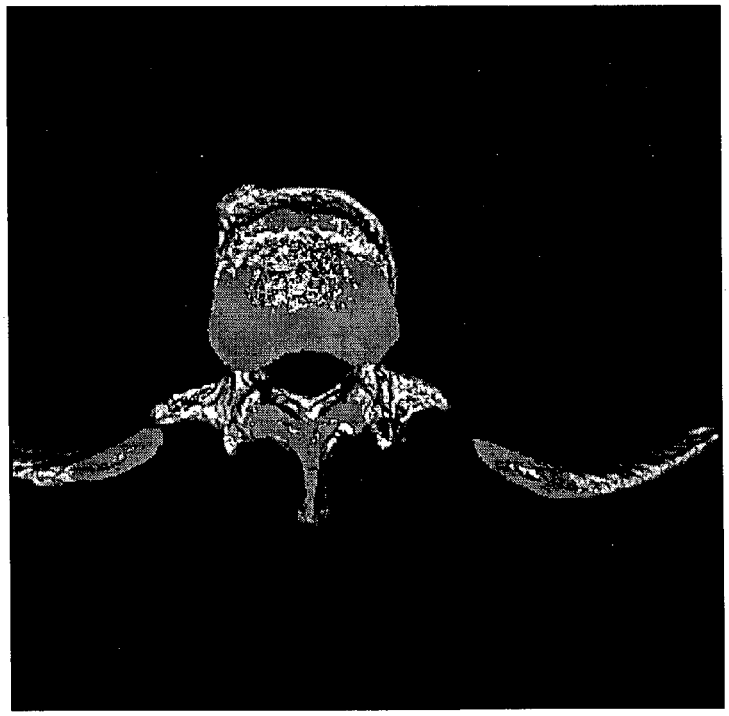
Figure 7:
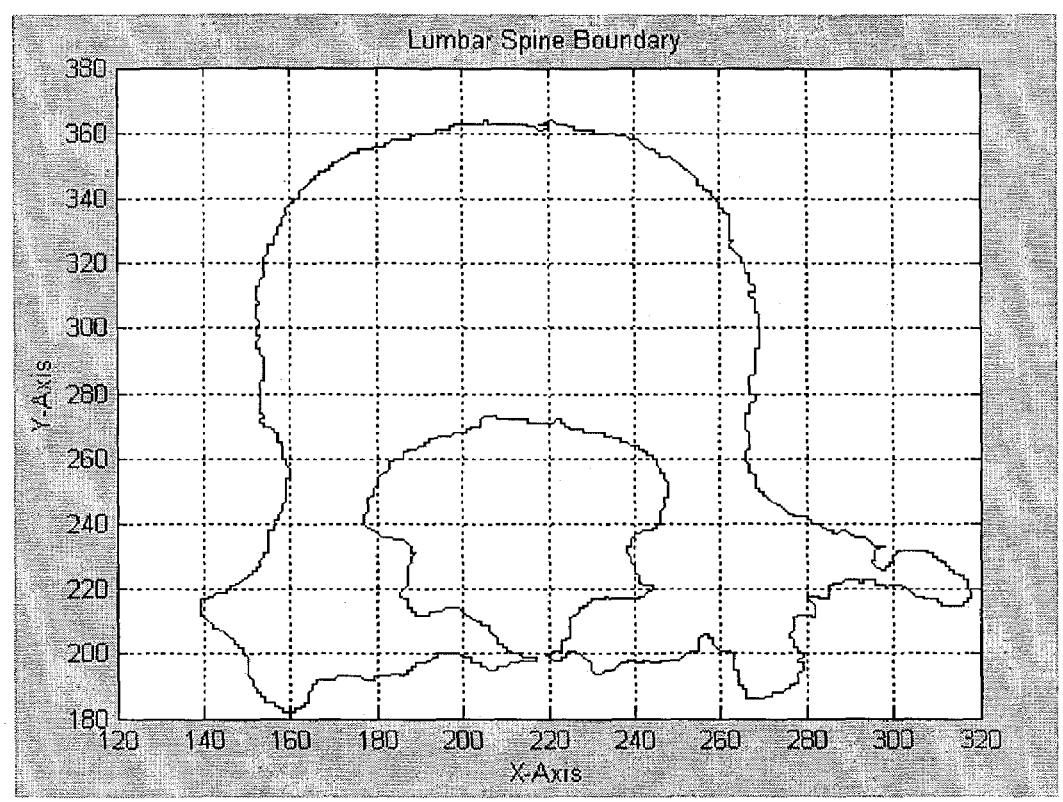
FIG. 7 depicts an example of the 2D boundary image.

A set of 2D images was imported into the software and a 3D volume was constructed based on the interpolation method described above. This volume is thresholded to yield the images shown in FIGS. 6a and 6b. A histogram of the volume gives a starting point for the segmentation threshold. The next step is to create the boundary of the segmented image that consists of the x and y locations of the boundaries for each slice. A 2D boundary image representation where the boundary points are connected using lines is shown in FIG. 7.

The method of the present invention in accordance with the algorithm starts by scanning through the boundary image from the top down. If the data are not oriented such that the vertebral body is located at the top of the image, the boundary image(s) may be rotated to orient the data correctly. As the scanning continues, there will be chords intersecting the boundaries. Initially, there are no points of intersection, and as the scanning progresses there appear chords with one, two, three, or more points of intersection. A chord that intersects four points is of interest because such chords will contain the inner and outer boundaries of the pedicles. Using this technique, the right and left pedicles may be identified.

Once the left and right pedicles have been identified, the pedicle widths may then be computed. Starting with a point on the "inner" pedicle curve for the left pedicle, one can compute the line segments (lengths) to the "outer" pedicle curve for all of the points on the outer pedicle curve. The minimum line length for the first point on the inner pedicle curve is stored. This procedure is repeated for all of the points on the inner pedicle curve to obtain the minimum length for each point on the inner pedicle curve of the left pedicle. The minimum transverse pedicle width for a particular slice is the minimum of these line lengths for the slice under study. This procedure is performed for both left and right pedicles for each image.

The same computation may be repeated for the remaining slices that make up the vertebra. The minimum of the minimum transverse pedicle widths is the overall minimum transverse pedicle width. The maximum pedicle screw width may be determined using the overall minimum transverse pedicle width. The overall minimum transverse pedicle width may also be used to define a diameter for a cylinder in the imaging planes that represents the pedicle screw diameter for the projection of the screw into the imaging planes (e.g., maximum diameter). Note that a scaling factor may be applied to the calculation so that an allowable or prescribed clearance may be specified between the inserted pedicle screw and the bone of the pedicle, e.g., multiply the overall minimum transverse pedicle width by a scaling factor less than one.

Figure 8:
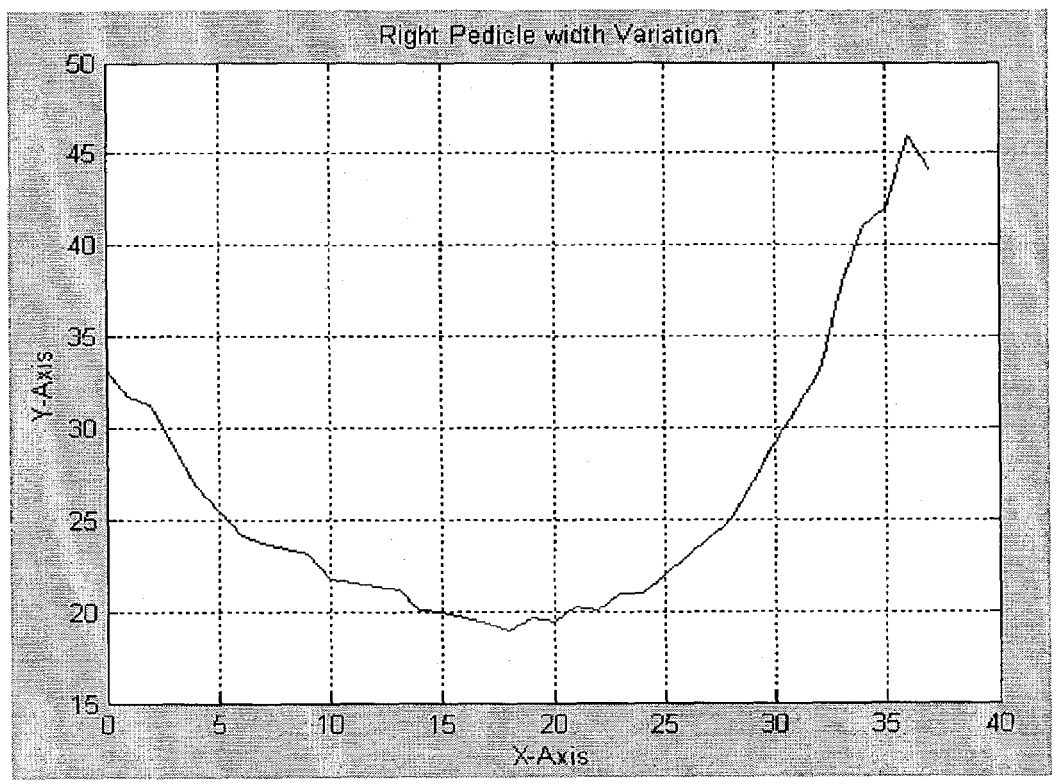
FIG. 8 depicts an example of the computed 2D widths between the pedicle boundaries for a single CT slide from which the minimum transverse pedicle width is determined for this slice of data.

The minimum transverse pedicle widths computed for a slice of data are shown in FIG. 8. Pixel length 18 from the y-axis corresponds to the overall minimum transverse pedicle width for the right pedicle in this slice, and this width corresponds to at least about 9 mm. Other methods may also be used to represent the image (e.g., quadtrees or octrees).

Figure 9:
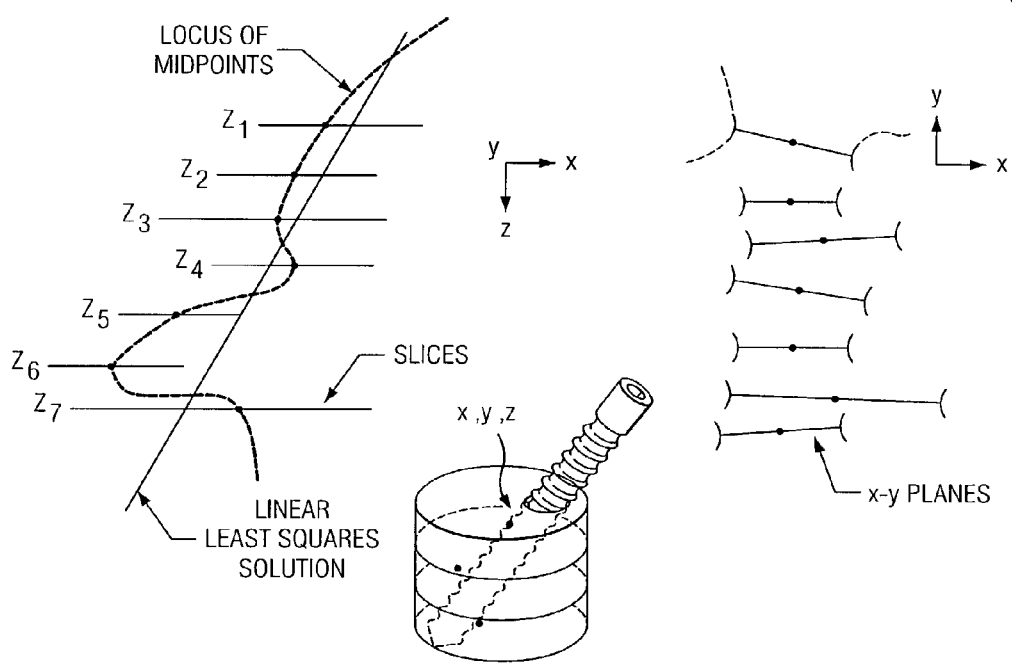
FIG. 9 depicts seven sample slices of an anatomic site as an example for the linear least squares solution and the optimum trajectory determination.
Figure 10:
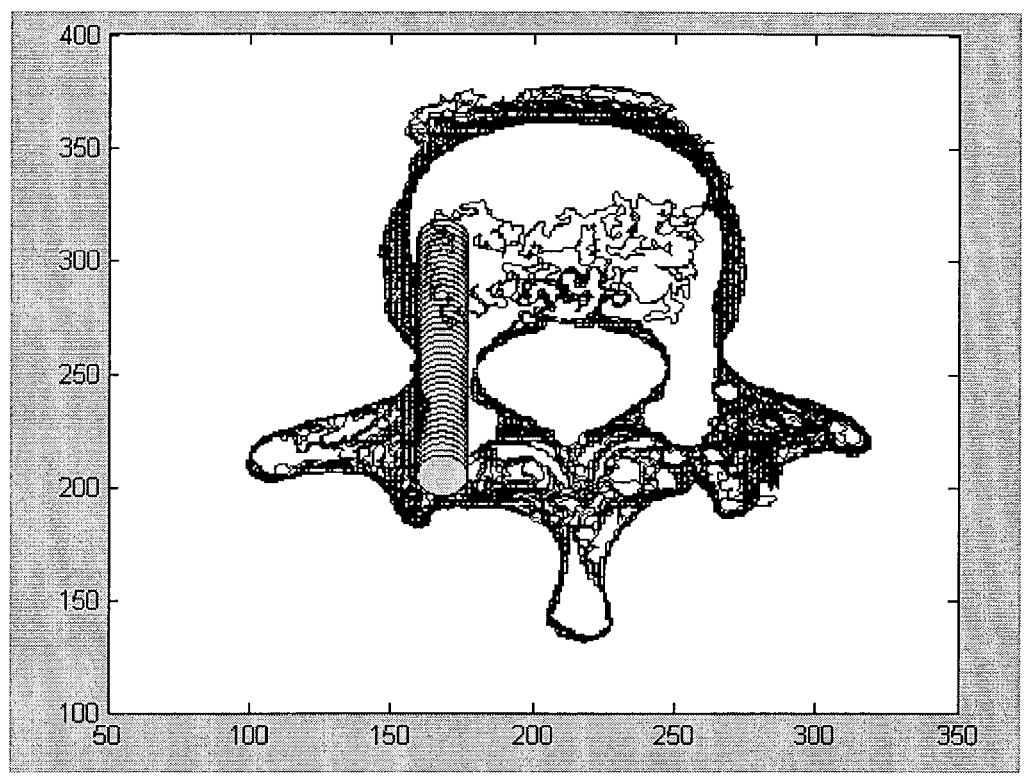
FIG. 10 depicts an example of the 3D approximation when planes are superimposed, wherein 2-D boundary images are superimposed to give a 3D approximation illustrating an optimum trajectory determination shown as superimposed disks (i.e., to simulate a pedicle screw).

To determine the optimum, the following method may be employed. For each slice, the coordinates (e.g., x, y, z), for the mid-points of the minimum transverse pedicle widths are calculated and stored, called, for example (x, y, z)$_{mid-point}$, as well as the coordinate, (x, y, z) $_{mid-point\ minimum}$, for the overall minimum transverse pedicle width. These points represent a locus of points used to determine the optimum trajectory by performing a linear least squares fit to the data, requiring the solution to go through the overall minimum transverse pedicle width located at (x, y, z) $_{mid\text{-}point,\ minimum}$. A simplified schematic illustrating this procedure is shown in FIG. 9 and a sample calculation is illustrated in FIG. 10 showing superimposed boundary images and a series of disks illustrating the optimum trajectory.

Once the optimum trajectory is determined, the x, y location of the linear least squares solution for each plane is calculated. Then, the radius for a circle with a diameter corresponding to the overall minimum transverse pedicle width and center located at the x,y location of the linear least square solution is used to test for interference with the boundaries on every slice. If no interference is identified, the solution is complete. If interference is identified, there are at least two possible paths to pursue. First, the calculated optimum trajectory may be retained and the radius can be reduced until interference has been eliminated. This radius corresponds to the maximum allowable radius in the imaging planes for the linear least squares optimum trajectory determination. If a screw of sufficient diameter for the medical procedure may be selected that has a projected diameter onto the imaging planes and is at least about less than or equal to twice the maximum allowable radius, the solution is complete. If not, an iterative weighted linear least squares solution may be performed to determine the maximum radius (or maximum diameter) cylinder that may traverse the pedicle in the imaging planes by iterating on the weight factors that apply to those slices where interference is identified. For this iterative procedure, the requirement of the trajectory going through the mid-point of the overall minimum transverse pedicle width may be relaxed.

Once the optimum trajectory is determined, the maximum length of bone (i.e., anatomic site used to determine implant length) may be determined by identifying the two points of intersection between the optimum trajectory line and the boundary images. The length of the line connecting these two points corresponds to the maximum length of bone for the optimum trajectory. With the optimum trajectory, overall minimum transverse pedicle width (or the maximum diameter cylinder that may traverse the pedicle in the imaging planes, depending on the interference test), and maximum length of bone determined, a suitable pedicle screw length and diameter and trajectory for the pedicle screw insertion medical procedure may be calculated by:

1. Selecting the maximum diameter screw that fits within the calculated overall minimum transverse pedicle width (or the maximum diameter cylinder that can traverse the pedicle in the imaging planes, depending on the interference test) with a pre-determined tolerance for the fit between the screw and the bone of the pedicle appropriately subtracted from this width and appropriately accounting for the projection of the screw diameter onto the imaging planes for the determination;

2. Determining the overall pedicle screw length as the calculated maximum length of bone for the optimum trajectory, subtracting a pre-determined tolerance for the fit between the end of the screw and the vertebral body, and adding the length of the screw that is required to be exposed for attaching additional instrumentation for fixation (such as a rod). This procedure can also be used to specify the length of drill bit to be used when drilling into the spine of a patient. The calculated drill bit length is the calculated maximum length of bone for the optimum trajectory less the pre-determined tolerance for the fit between the end of the screw and the vertebral body; and 3. The optimum trajectory is determined as described above. This trajectory is a line of the form $z = Ax + By + C$, and may be represented in any coordinate system, although it is initially represented in the coordinate system as originally provided by the medical imaging scan. The trajectory can be provided relative to any landmark used in the medical procedure. The process is repeated for all components of the implant and/or device using one or more anatomic sites, as required. One of ordinary skill in the art will know the anatomic sites of interest.

As such, the present invention enables a user to rapidly and accurately define the best location for one or more implants or devices at one or more anatomic sites. For example, with the present invention, it is possible to consistently and reproducibly obtain the optimum path for a pedical screw that inserts into a vertebra prior to surgery. Any or all of the steps discussed above are repeated to acquire all the required paths for proper placement of one or more implants. Proper placement is thus modeled to an individual based on his/her unique anatomy. A generalized method of acquiring data may be obtained with the use of one or more cadavers. Alternatively, a method of patient typing may be created (such as one that is based on a set of generalized anatomic criteria).

In one embodiment of the present invention, simulations enable a user to test one or more implants and/or devices. Simulations may also be automated. A predetermined set of data may be provided for one or more users and/or for one or more tasks and used for repetitive guidance and learning. As used herein, simulations require the use of a processor, such as a fixed or mobile computer and may include a processor linked to a network for multi-use or multi-user applications. Importantly, calculations of the present invention may be repeated indefinitely using varying anatomic and implant parameters. The utility of this is especially suited for teaching and training purposes (e.g., for the healthcare and engineering industries), for modeling, for research and development, for screening and testing, and other medical, technologic or industrial applications. For use in modeling and manufacturing, an initial reference system may be used based on a set of predetermined points of interest. As previously discussed, other applications for which the present invention is useful include, but are not limited to, automated tasking, robotics, robot-assisted and computer-assisted surgery, as examples.

Further, in accordance with another aspect of the present invention, a computer system for determining pedicle screw placement is provided, wherein the computer system includes a processor to receive imaging data and to use the data to calculate the optimum trajectory and the depth and diameter of a pedicle screw path within the bony structure, wherein the imaging data includes an image of a bony structure.

Still in another aspect of the present invention, a method for determining the placement of an implant in a patient in need thereof is provided by analyzing intensity-based medical imaging data obtained from a patient, isolating an anatomic site of interest from the imaging data, and determining anatomic spatial relationships within the an algorithm.

Still another embodiment of the present invention is method in accordance with an algorithm comprising the following steps of importing data collected from one or more images of an anatomic site, pre-processing the data to ensure compatibility with an algorithm, isolating the anatomic area of interest using a thresholding segmentation algorithm, defining the boundaries of the anatomic site for each calculated plane, and computing a series of calculations based on the anatomic site and the implant to extract information about placement of the implant at the anatomic site.

Additional objects, advantages and novel features of the invention as set forth in the description that follows, will be apparent to one skilled in the art after reading the foregoing detailed description or may be learned by practice of the invention. The objects and advantages of the invention may be realized and attained by means of the instruments and combinations particularly pointed out here.

What is claimed is:

1. A method for determining an optimal placement of a pedicle screw in a patient from imaging data obtained from a medical imaging device, comprising:
    receiving medical imaging data that includes one or more images of a bony structure of a spine of the patient;
    determining surface boundaries of the bony structure for one or more of the images; and
    calculating an optimal trajectory of the pedicle screw having a predetermined initial diameter within the surface boundaries, wherein the optimal trajectory is automatically calculated to be within the surface boundaries by a computer processor performing an algorithm mathematically comparing the surface boundaries on a computer.

2. The method of claim 1, further comprising calculating an optimal diameter of the pedicle screw to replace the predetermined initial diameter, wherein the optimal diameter is automatically calculated to be within the surface boundaries by the computer processor performing the algorithm mathematically comparing the surface boundaries on the computer.

3. The method of claim 1, further comprising calculating an optimal depth to insert the pedicle screw, wherein the optimal depth is calculated by the computer processor performing a second algorithm on the computer.

4. The method of claim 1, wherein the medical imaging data comprise intensity-based imaging data.

5. The method of claim 1, wherein the medical imaging data are chosen from the group consisting of computed tomography data, positron emission tomography data, ultrasound data, and magnetic resonance imaging data.

6. The method of claim 1, further comprising analyzing the medical imaging data to determine if the algorithm is compatible with the imaging data.

7. The method of claim 1, wherein the determining surface boundaries comprises:
    isolating the bony structure of the spine of the patient from the medical imaging data; and
    determining the minimum thickness of a spinal pedicle, a pedicle length, and an orientation to the spine of the patient.

8. The method of claim 1, wherein calculating the optimum trajectory includes performing a least squares fit or weighted least squares fit on a locus of mid-points for minimum transverse pedicle widths of one or more of the images.

9. A computer system for determining an optimal placement of a pedicle screw in a patient from imaging data obtained from a medical imaging device, comprising:
    one or more process; and
    a computer readable medium connected to the processors, the computer readable medium including processor instructions configured to be read by the processors and thereby cause the processors to:
    receive medical imaging data that includes one or more images of a bony structure of a spine of the patient;
    determine surface boundaries of the bony structure for one or more of the images;
    calculate an optimal trajectory, an optimal diameter and an optimal depth of the pedicle screw within the surface boundaries, wherein the optimal trajectory. the optimal diameter and the optimal depth are automatically calculated to be within the surface boundaries by mathematically comparing the surface boundaries; and
    output of the optimal trajectory, the optimal diameter and the optimal depth.

10. The computer system of claim 9, wherein the processor instructions are further configured to be read by the processors and thereby cause the processors to:
    interpolate the imaging data;
    segment the interpolated imaging data;
    extract a boundary of the bony structure from the interpolated imaging data;
    identify a pedicle from the extracted boundary; and
    calculate a minimum pedicle width, a maximum depth and a direction of the pedicle based on the coordinate system of the medical imaging data.

11. The computer system of claim 9, wherein calculating the optimum trajectory includes performing a least squares fit or weighted least squares fit on a locus of mid-points for minimum transverse pedicle widths of one or more of the images.

12. The computer system of claim 9, wherein the optimal trajectory, the optimal diameter and the optimal depth are output to a robotic device.

13. The computer system of claim 9, wherein the optimal trajectory, the optimal diameter and the optimal depth are output on a computer display.

14. The computer system of claim 9, wherein the optimal trajectory, the optimal diameter and the optimal depth are output to another computer system.

15. A computer system for determining an optimal placement of a pedicle screw in a patient from imaging data obtained from a medical imaging device, comprising:
    one or more processors; and
    a computer readable medium connected to the processors, the computer readable medium including processor instructions configured to be read by the processors and thereby cause the processors to:
    receive medical imaging data that includes one or more images of a bony structure of a spine of the patient;
    determine surface boundaries of the bony structure for one or more of the images;
    calculate an optimal trajectory and an optimal diameter of the pedicle screw within the surface boundaries, wherein the optimal trajectory and the optimal diameter are automatically calculated to be within the surface boundaries by mathematically comparing the surface boundaries; and
    output of the optimal trajectory and the optimal diameter.

16. The computer system of claim 15, wherein the optimal trajectory and the optimal diameter are output to a robotic device.

17. The computer system of claim 15, wherein the optimal trajectory and the optimal diameter are output on a computer display.

18. The computer system of claim 15, wherein the optimal trajectory and the optimal diameter are output to another computer system.

19. A method for determining an optimal placement of an implant in a patient comprising:
    receiving medical imaging data that includes one or more intensity-based images of the patient;

analyzing the medical imaging data;

isolating an anatomic site of interest from the medical imaging data;

determining anatomic spatial relationships from the medical imaging data to identify the optimal placement of the implant, wherein the determining includes a determination of a minimum thickness of the anatomic site, a length of the anatomic site, and an orientation to the anatomic site relative to the orientation of the patient; and calculating an optimal trajectory of the pedicle screw having a predetermined initial diameter within the anatomic site, wherein the optimal trajectory is automatically calculated by a computer processor performing an algorithm mathematically comparing the anatomic spatial relationships on a computer.

20. The method of claim 19, further comprising calculating an optimal diameter of the implant to replace the predetermined initial diameter, wherein the optimal diameter is automatically calculated to be within the surface boundaries by the computer processor performing the algorithm mathematically comparing the surface boundaries on the computer.

21. The method of claim 19, further comprising calculating an optimal depth to insert the implant, wherein the optimal depth is calculated by a computer processor performing a second algorithm on the computer.

22. The method of claim 19, wherein the medical imaging data are chosen from the group consisting of computed tomography data, positron emission tomography data, ultrasound data, and magnetic resonance imaging data.

23. The method of claim 19, further comprising analyzing the medical imaging data to determine if the algorithm is compatible with the medical imaging data.

24. A method for determining an optimal trajectory of an implant at an anatomic area of a patient, comprising:

receiving medical imaging data that includes one or more images of an anatomic site of the patient;

pre-processing the medical imaging data to ensure compatibility with an algorithm;

isolating an anatomic area of interest from the medical imaging data using a thresholding segmentation algorithm;

defining boundaries of the anatomic area in three-dimensions; and calculating the optimal trajectory of the implant at the anatomic site using search calculations based on the anatomic site and the implant, wherein the optimal trajectory is automatically calculated by a computer processor performing the algorithm mathematically comparing the boundaries on a computer.

25. The method of claim 24, wherein the calculating includes calculations chosen from the group consisting of a minimum anatomic diameter, a maximum implant diameter, an optimum implant trajectory, a maximum length of the anatomic site, an optimum length of the implant, and combinations thereof.

26. The method of claim 25, wherein the calculations are search algorithms that include geometric considerations.

27. A computer program embodied in a computer readable medium for performing a determination of an optimal trajectory of an implant at an anatomic area of a patient from imaging data obtained from a medical imaging device, comprising:

a first computer code for receiving medical imaging data collected from one or more images of an anatomic site of the patient;

a second computer code for isolating an anatomic area of interest from one or more of the images using thresholding segmentation;

a third computer code for determining boundaries of the anatomic area of interest in three-dimensions;

a fourth computer code for calculating the optimal trajectory of the implant at the anatomic area based on the anatomic area and the implant, wherein the optimal trajectory is automatically calculated by mathematically comparing the boundaries; and a fifth computer code for outputting the optimal trajectory.

28. The computer program of claim 27, wherein the fourth computer code includes calculations that comprise at least one of a minimum anatomic diameter, a maximum implant diameter, an optimum implant trajectory, a maximum length of the anatomic site, and an optimum length of the implant.

29. The computer program of claim 27, wherein medical imaging data are chosen from the group consisting of computed tomography data, positron emission tomography data, ultrasound data, and magnetic resonance imaging data.

30. The computer program of claim 29, further comprising a sixth computer code for initially pre-processing the medical imaging data.

31. The computer program of claim 30, wherein the sixth computer code comprises standardizing medical imaging data acquired from different medical imaging devices.

32. The computer program of claim 31, wherein standardizing medical image data comprises standardizing at least one of a pedicle length, a pedicle length, and a pedicle trajectory.

33. The computer program of claim 32, wherein the medical imaging data comprises two-dimensional data collected from a plurality two-dimensional image scans of the anatomic site.

34. The computer program of claim 33, wherein one or more of the plurality two-dimensional image scans have differing interslice distances, the sixth computer code for pre-processing the data further comprises a seventh computer code for interpolating one of the three-dimensions to equalize the interslice distances.

35. The computer program of claim 27, wherein the optimal trajectory is output to a robotic device.

36. The computer program of claim 27, wherein the optimal trajectory is output on a computer display.

37. The computer program of claim 27, wherein the optimal trajectory is output to another computer system.

* * * * *